(12) United States Patent
Boul et al.

(10) Patent No.: US 11,280,713 B2
(45) Date of Patent: Mar. 22, 2022

(54) TESTING CEMENT SHEAR BOND STRENGTH AT RESERVOIR CONDITIONS

(71) Applicant: Saudi Arabian Oil Company, Dhahran (SA)

(72) Inventors: Peter Boul, Houston, TX (US); Arpita Pal Bathija, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 104 days.

(21) Appl. No.: 16/831,660

(22) Filed: Mar. 26, 2020

(65) Prior Publication Data

US 2021/0302292 A1     Sep. 30, 2021

(51) Int. Cl.
| | |
|---|---|
| *G01N 3/06* | (2006.01) |
| *G01N 29/07* | (2006.01) |
| *G01N 29/12* | (2006.01) |
| *G01N 29/14* | (2006.01) |
| *G01N 33/38* | (2006.01) |
| *G01N 3/24* | (2006.01) |

(52) U.S. Cl.
CPC .............. *G01N 3/24* (2013.01); *G01N 3/066* (2013.01); *G01N 29/07* (2013.01); *G01N 29/12* (2013.01); *G01N 29/14* (2013.01); *G01N 33/383* (2013.01); *G01N 2203/0025* (2013.01); *G01N 2203/0064* (2013.01); *G01N 2203/0256* (2013.01); *G01N 2291/014* (2013.01); *G01N 2291/0232* (2013.01); *G01N 2291/0289* (2013.01); *G01N 2291/106* (2013.01)

(58) Field of Classification Search
CPC ........ G01N 29/34; G01N 29/07; G01N 3/066; G01N 33/383; G01N 29/14; G01N 29/12; G01N 2291/106; G01N 2291/0232; G01N 2203/0256; G01N 2291/014; G01N 2203/0025; G01N 2203/0064; G01N 2291/0289
USPC ............................................................ 73/582
See application file for complete search history.

(56) References Cited

U.S. PATENT DOCUMENTS

| | | | |
|---|---|---|---|
| 5,159,828 A | * | 11/1992 | Steiger ................. E21B 49/006 73/38 |
| 6,324,916 B1 | | 12/2001 | Jessop |
| 6,609,067 B2 | * | 8/2003 | Tare ......................... E21B 21/08 702/9 |
| 7,525,872 B2 | | 4/2009 | Tang et al. |

(Continued)

FOREIGN PATENT DOCUMENTS

| | | |
|---|---|---|
| EP | 2820413 | 1/2015 |
| EP | 3060909 | 8/2016 |

OTHER PUBLICATIONS

U.S. Appl. No. 16/393,016, Hakimudding et al., filed Apr. 24, 2019.

(Continued)

*Primary Examiner* — Jacques M Saint Surin
(74) *Attorney, Agent, or Firm* — Fish & Richardson P.C.

(57) ABSTRACT

Systems and methods for testing shear bond strength of cement with a composite sample under downhole conditions form a bonding surface of the sample oriented at an angle between 50 and 70 degrees from a plane perpendicular to a longitudinal axis of the sample. The composite sample is formed by bonding the cement to the sample with the cement in contact with the bonding surface of the sample.

26 Claims, 11 Drawing Sheets

(56) References Cited

U.S. PATENT DOCUMENTS

| | | | |
|---|---|---|---|
| 7,555,414 B2 * | 6/2009 | Calhoun | E21B 49/006 |
| | | | 703/2 |
| 7,773,454 B2 | 8/2010 | Barolak et al. | |
| 7,787,327 B2 | 8/2010 | Tang et al. | |
| 8,770,038 B2 * | 7/2014 | Secq | G01N 3/24 |
| | | | 73/821 |
| 9,228,993 B2 | 1/2016 | Shine et al. | |
| 10,048,336 B2 * | 8/2018 | Hakimuddin | G01R 33/305 |
| 2015/0061669 A1 * | 3/2015 | Hakimuddin | G01R 33/28 |
| | | | 324/309 |
| 2015/0152724 A1 | 6/2015 | Amendt et al. | |
| 2018/0335494 A1 * | 11/2018 | Hakimuddin | G01N 24/081 |
| 2020/0070179 A1 * | 3/2020 | Hakimuddin | G01N 33/24 |
| 2020/0340895 A1 * | 10/2020 | Hakimuddin | G01N 15/082 |

OTHER PUBLICATIONS

API, "10B-2, Recommended Practice for Testing Well Cements," American Petroleum Institute, 1-124, RP 10B-2, Apr. 2019, 124 pages.

Liu et al., "A novel method to evaluate cement shale bond strength," SPE International Symposium on Oilfield Chemistry, SPE-173802-MS, Apr. 13-15, 2015, 20 pages.

Opedal et al., "Experimental study on the cement-formation bonding," SPE International Symposium and Exhibition on Formation Damage Control, Feb. 26-28, 2014, 12 pages.

Radonjic and Oyibo, "Experimental evaluation of wellbore cement-formation shear bond strength in presence of drilling fluid contamination," International Conference on porous media and their applications in science, engineering and industry, Hawaii, Jun. 24, 2014, 7 pages.

Zoback, "Reservoir geomechanics," Cambridge University Press, 2010, 2 pages.

Carey et al., "Fracture-permeability behavior of shale." Journal of unconventional oil and gas resources 11, Sep. 2015, 53 pages.

Genedy et al., "Examining epoxy-based nanocomposites in wellbore seal repair for effective CO2 sequestration," Energy Procedia 63, Jan. 2014, 5798-5807, 10 pages.

Isaka et al., "Influence of long-term operation of supercritical carbon dioxide based enhanced geothermal system on mineralogical and microstructurally-induced mechanical alteration of surrounding rock mass." Renewable Energy 136, Jun. 2019, 14 pages.

Kuo et al., "Bonding behavior of repair material using fly-ash/ground granulated blast furnace slag-based geopolymer," Materials 12.10, Jan. 2019, 16 pages.

Welch et al., "Shear strength and permeability of the cement-casing interface." International Journal of Greenhouse Gas Control 95, Apr. 2020, 29 pages.

PCT International Search Report and Written Opinion in International Appln. No. PCT/US2021/024111, dated Jul. 2, 2021, 17 pages.

* cited by examiner

TESTING CEMENT SHEAR BOND STRENGTH AT RESERVOIR CONDITIONS

TECHNICAL FIELD

This disclosure relates to the determination of physical properties including shear bond strength of cement.

BACKGROUND

Mechanical properties of materials, such as rocks, metals, and concrete, are used in research, design, and analysis in many engineering and science industries. In a drilling environment, it is important to evaluate the bond strength of cement with the casing materials and the subterranean formations at reservoir conditions. Testing of such materials typically involves using a tri-axial testing system to measure mechanical properties.

SUMMARY

This specification describes testing systems and methods that can used for evaluating new or improved cements for specific subterranean formations. These system and methods use a combination of acoustic and stress sensors to provide consistent measurements of shear bond strength. The incorporation of acoustic sensors provides additional data for identifying, for example, failure of the bond between a cement and a primary sample rather than just providing a single number to define the shear bond strength.

Methods for testing shear bond strength of cement with a sample under downhole conditions can include: forming a bonding surface of the sample oriented at an angle between 50 and 70 degrees from a plane perpendicular to a longitudinal axis of the sample; forming a composite sample by bonding the cement to the sample with the cement in contact with the bonding surface of the sample; installing the composite sample in a cell casing; installing the cell casing in a tri-axial testing machine; applying a first pressure to the composite sample, wherein the first pressure is greater than an environmental pressure; and applying an axial pressure to the cell casing and sample that is greater than the first pressure.

Systems for testing a composite sample formed of a cement bonded with a primary sample to identify a shear bond strength of the cement with the primary sample can include: a first acoustic transducer; a second acoustic transducer; a third acoustic transducer; and a strain gauge; wherein the first acoustic transducer and the second acoustic transducer is configured to measure p wave velocity or s wave velocity; and wherein the third acoustic transducer is passive and configured to listen for acoustic emissions.

Embodiments of these systems and methods can include one or more of the following features.

Some embodiments also include coating the sample with a drilling fluid before forming the composite sample.

Some embodiments also include measuring a p wave velocity or an s wave velocity of the composite sample using a first acoustic transducer and a second acoustic transducer.

Some embodiments also include measuring an intensity, frequency, or dispersion of acoustic waves emitted by the composite sample using a third acoustic emission transducer. In some cases, embodiments include identifying an initial compaction phase of axial compression by detecting an increase in acoustic emissions relative to an ambient condition and an increase in pressure wave velocity, shear wave velocity, or both. In some cases, embodiments include identifying a quasi-linear elastic phase of the axial compression by detecting a decrease in acoustic emissions and a decrease in a rate of increase of wave velocity using the first acoustic transducer and the second acoustic transducer. In some cases, embodiments include identifying a micro-crack initiation and extension phase of the axial compression by detecting an increase in acoustic emissions. In some cases, embodiments include identifying a crack coalescence and dynamic failure phase of the axial compression by detecting an increase in acoustic emissions and a decrease in a p wave velocity and an s wave velocity using the first acoustic transducer and the second acoustic transducer. In some cases, embodiments include identifying a frictional sliding phase by detecting a decrease in a load bearing capacity of the composite sample, an increase in acoustic emissions, or both. In some cases, embodiments include measuring a strain of the composite sample using a strain gauge located on the composite sample. In some cases, embodiments include determining the shear bond strength of cement.

Some embodiments also include forming the composite sample comprises trimming the lower end surface to be flat and perpendicular to the longitudinal axis.

In some embodiments, forming the composite sample comprises trimming the composite sample to achieve a length of the composite sample to a diameter of the composite sample ratio greater than or equal to 2.

In some embodiments, forming the composite sample comprises trimming the composite sample to be 40-60% cement and 40-60% sample.

Some embodiments also include a first end cap attachable to the composite sample with the first acoustic transducer mounted on the first end cap. Some embodiments also include a second end cap attachable to the composite sample with the second acoustic transducer mounted on the second end cap.

In some embodiments, the first acoustic transducer is configured to transmit a signal and the second acoustic transducer is configured to receive the signal. Some embodiments also include a cylindrical casing. In some embodiments, the third acoustic transducer is also mounted on the first end cap. In some embodiments, the strain gauge is located on outer surface of the cylindrical casing.

In some situations, these systems and methods are easier to use and provide more consistent results than conventional push-out testing. For example, conventional push-out testing is difficult to use for weaker or laminated rocks and does not provide consistent results because the formation sample may fail structurally before the bond between the sample and the cement fails.

The details of one or more embodiments of these systems and methods are set forth in the accompanying drawings and the description below. Other features, objects, and advantages of these systems and methods will be apparent from the description and drawings, and from the claims.

DESCRIPTION OF DRAWINGS

Like reference symbols in the various drawings indicate like elements.

DETAILED DESCRIPTION

The present disclosure is directed to systems and methods for characterizing the shear bond strength of cement, for example, to subterranean formations or wellbore casings. These systems and methods can be used for testing various cement formulations with additives and drilling fluids on various subterranean formations and casing materials. For example, cement is often used during drilling operations and it is important to understand the shear bond strength of the cement to the surrounding subterranean formations. This interaction can fail to provide zonal isolation leading to a wellbore control hazard or loss of production. The cement to formation interface can fail in shear due to the stresses induced during drilling, completion/stimulation or production phases of wellfield operations. For example, downhole reservoir conditions can give rise to very large volumetric and axial stresses in materials. In developing improved cements for effective zonal isolation, it is important to evaluate the bond strength of the cement-to-formation interface under conditions that approximate the downhole environment.

One way to test this bond strength is to extract a core sample of the subterranean formation, bond it to cement (forming a composite sample of the core sample and the cement) and perform tri-axial stress testing to establish bond failure. In tri-axial shear testing, stress is applied to the composite sample with stresses along one axis being different from the stresses in perpendicular directions. The application of different compressive stresses in the tri-axial test apparatus causes shear stress to develop in the composite sample with loads being increased and deflections monitored until failure of the sample occurs. The loads at failure are characteristic of shear bond strength.

Figure 1:
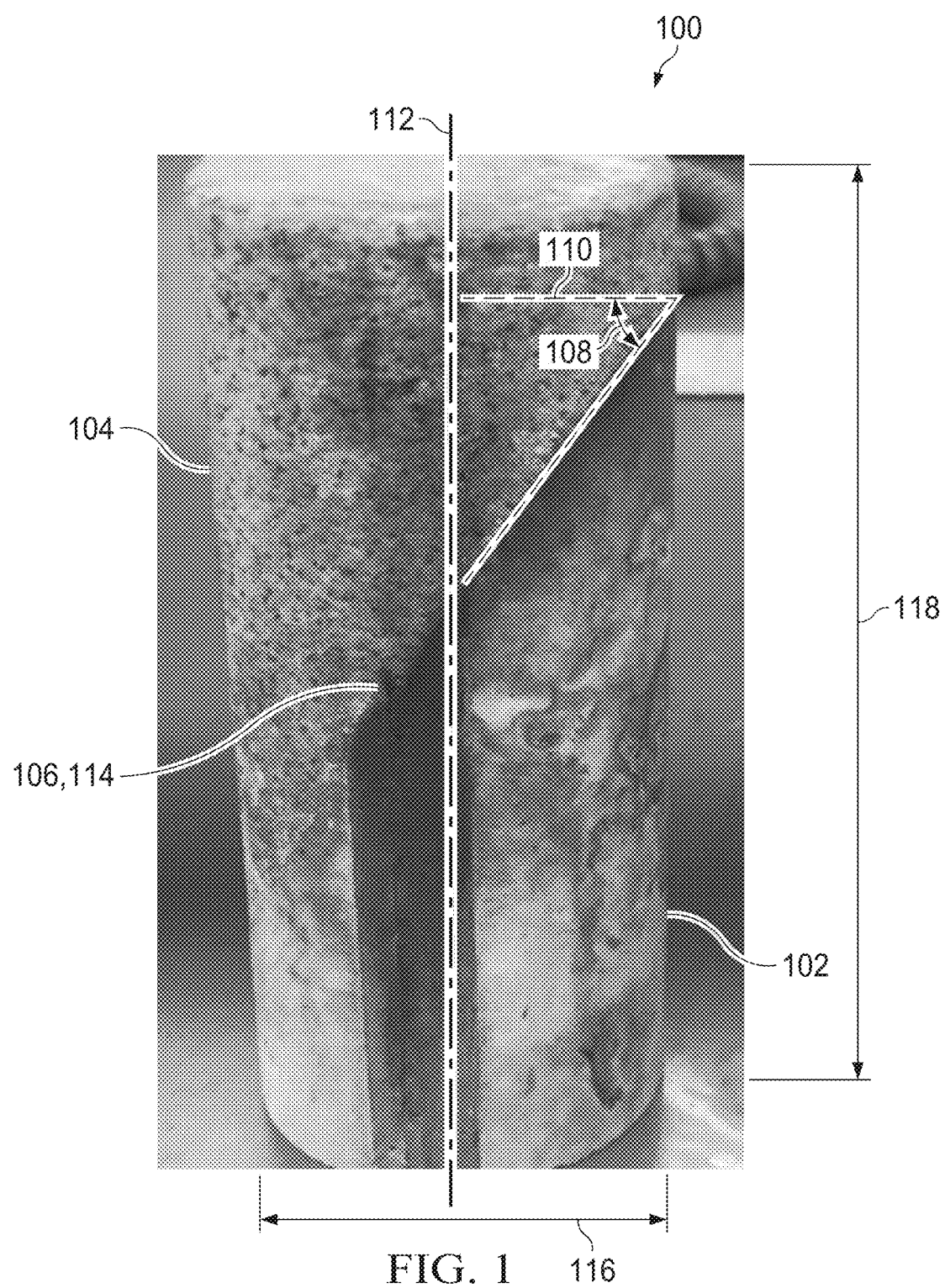
FIG. 1 is a photograph of a cement-sandstone composite sample.

FIG. 1 shows a composite sample 100 of cement 102 and a primary sample. In this case, the primary sample is sandstone 104. The cement 102 and the sandstone 104 are bonded together at a bond plane 106 oriented at a 60 degree angle 108 measured from a plane 110 perpendicular to a longitudinal axis 112 of the composite sample 100. Rock theory estimates the degree to which bedding planes lower the rock strength mathematically. According to rock theory, by bonding cement 102 to the sandstone 104 at a bond plane 106 oriented at a 60-degree angle 108, slip on a bedding plane will occur at a lower stress level than that required to form a new fault. This is advantageous during testing where lower loads are needed to induce failure. Setting the bond plane 106 between the cement 102 and the sandstone 104 at a 60-degree angle 108 is easier, faster, more repeatable, and cheaper since it uses less material than conventional push-out testing.

Measuring the shear bond strength at the bond plane 106 along with velocities, acoustic emissions and other properties at downhole reservoir conditions provides more than just a number to define the shear bond strength at the bond plane 106 between the cement 102 and the sandstone 104. This testing and measurement approach can provide fast quantitative evaluation of new cement formulations in the laboratory. One advantage of this method is an ability perform a controlled study by changing the bond plane 106 interface by adding various drilling fluids. For example, by introducing a drilling fluid to the core sample, the bond strength can be altered. In some cases, the shear bond strength can be reduced by approximately 50% when oil based mud is introduced at the interface. This will be discussed in further detail with reference to FIG. 3.

In addition to testing the shear bond strength of cement to a core sample, this approach can be used to test the shear bond strength of cement to a casing material, such as carbon steel. Bonding to a casing material is often just as important as bonding to subterranean formations. When cement is used in a wellbore, it is often bonded to both the neighboring subterranean formation and to casing material lining the wellbore. Referring back to FIG. 1, a composite sample with casing material rather than the sandstone 104 as the primary sample can be used to study the cement-casing shear bond strength.

Figure 2:
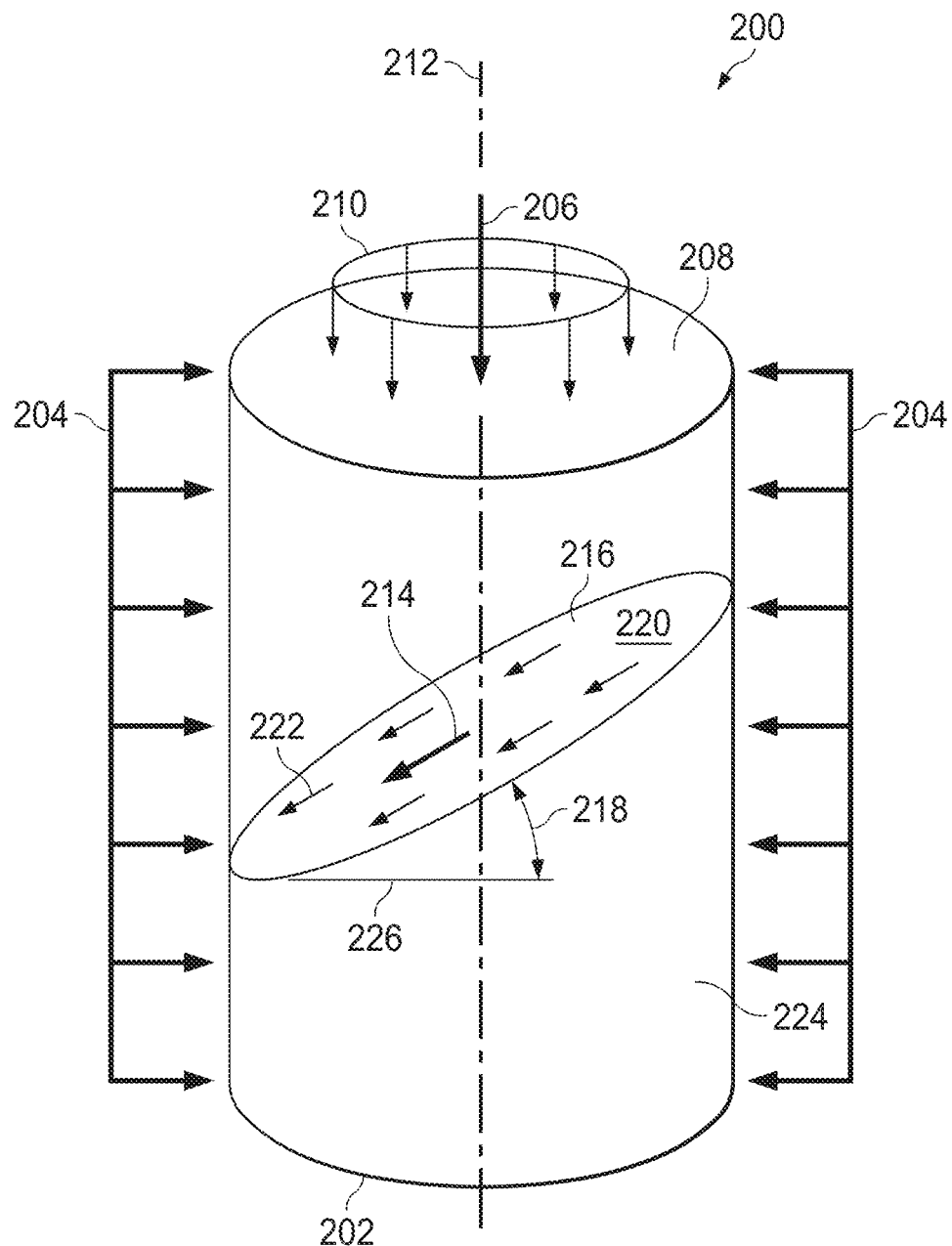
FIG. 2 a schematic illustrating stresses at reservoir conditions.

FIG. 2 shows a stress state in a material 202 being tested at downhole reservoir conditions 200. The material need not be a composite for this stress state to be achieved. A homogeneous material will also have this stress state at downhole reservoir conditions. A confining pressure 204 develops from burial under the ground and an overburden pressure 206 develops on the top surface 208 of the sample. This overburden pressure 206 is considered to be an applied axial stress 210 on the material because it aligns with a longitudinal axis 212 or axial direction of the sample. A stress state with a confining pressure circumferentially all round and axial stress in vertical direction is achieved. This combined stress state gives rise to regions of shear stress within the material.

As further shown in FIG. 2, given an axial force F1 206 acting on a surface 208 of the material having an area A1 208, one can determine the axial stress S1 210, also referred to as normal stress, as S1=F1/A1. The shear force F2 214 at a plane 216 denoted by radian angle BETA 218 can be determined from the axial force as $$F2 = F1*\mathrm{SIN}(BETA) \qquad \mathrm{Eq.~(1)}$$

The area 220 of the plane 216 that the shear force acts is $$A2 = A1/\mathrm{COS}(BETA) \qquad \mathrm{Eq.~(2)}$$

The shear stress S2 222 that develops is $$S2 = F2/A2 = S1*\mathrm{SIN}(BETA)*\mathrm{COS}(BETA) \qquad \mathrm{Eq.~(3)}$$

The confining pressure 204 (also known as confining stress) S3 is applied directly to the outer cylindrical surface 224. Hence, for a given F1 force, shear stress S2 is at a maximum along a plane 216 oriented an angle BETA 218 of 60 degrees from the horizontal 226. Therefore, designing a composite sample, such as the composite sample 100, that is bonded at a plane 106 oriented at an angle of 60 degrees 108 from a transverse plane 110, when loaded with a confining pressure 204 under these conditions will require less of an axial force

206 to cause shear bond failure than a composite sample bonded at a bond plane oriented at other angles. Even though confining pressure 204 S3 does not appear in Eqs. (1)-(3), it can affect the shear failure results. Increasing the confining pressure 204 S3 increases the strength of the material so that a larger peak force F1 is needed to induce shear failure of the material.

Referring back to FIG. 1, a composite sample is formed with a material to be bonded to a cement (i.e., the primary sample) having a face with an angle to a transverse plane of the material of between 50 and 70 degrees (e.g., between 55 and 65 degrees). For example, the primary sample shown in FIG. 1 was formed by cutting a core sample of a subterranean formation (e.g., the sandstone core sample 104) at a plane 106 oriented at a 60 degrees angle 108 from transverse plane 110. This cutting operation is performed using a set, or constant, cutting speed to control the surface roughness of the bonding interface 114. The angle is preferably 60 degrees but may deviate due to angular misalignment of the cutting equipment and surface roughness of the bonding interface 114. For example, the core sample 104 can be cut at an angle 108 of 55 degrees or an angle 108 of 65 degrees. The core sample 104 is typically 1-2 inches in diameter 116 and 3-5 inches in axial length 118. For example, the core sample may be 1.5 inches in diameter 116 and 4 inches in length 118. Keeping the length to diameter ratio of the core sample constant usually helps obtain consistent results. The surface roughness at the bonding interface 114 can be verified with optical profiler. Typical values for Berea sandstone roughness is 230 micrometers but it can be polished to have a smooth surface. Rough surfaces can give better adhesion and hence higher shear bond strength. Similar to size constraints, it is important to compare the shear bond strengths of similar material with similar roughness.

Figure 3:
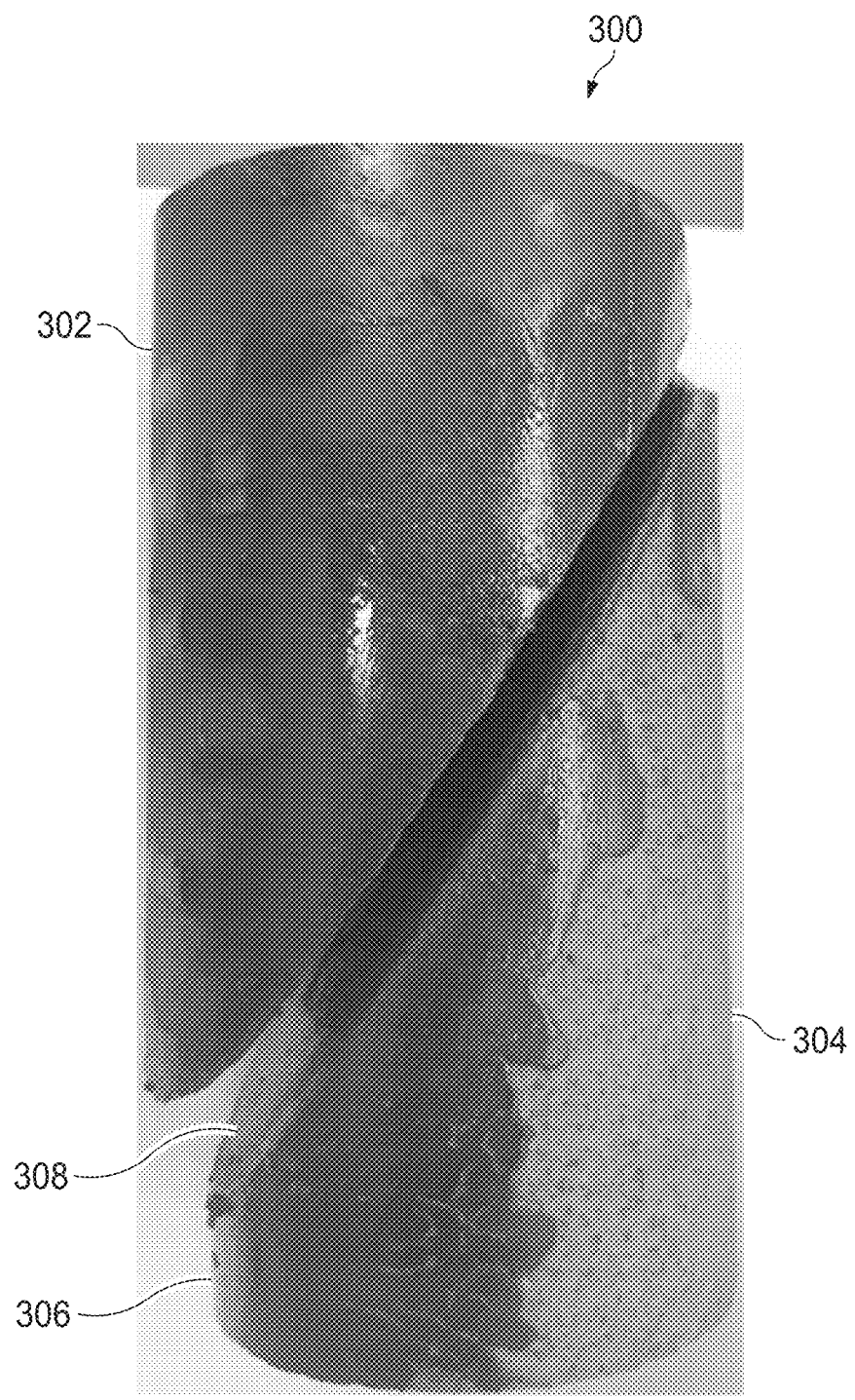
FIG. 3 is photograph of a cement-sandstone composite sample with oil-based mud applied at the bonding interface.

These system and methods can also be used to evaluate the effect of drilling fluid, and its coating thickness, on the shear bond strength at the interface between the cement and the primary sample. This is shown in FIG. 3 for a composite sample 300 formed from a cement 302 and a sandstone 304. Drilling fluid 306 (e.g., an oil-based mud, water-based mud, or either of these with other additives) is shown at the interface 308 between the sandstone 304 and the cement 302. To achieve a uniform coating at the interface, the inclined surfaces of the primary sample can be dipped in drilling fluid and then hung to drip off excess fluid. The penetration of the drilling fluid into a subterranean formation can impact the shear bond strength of cement to the formation. The permeability of the sample will determine how quickly the fluid will penetrate into the formation. Consistency can often be important here, since similar core samples with different soaking times for drilling fluid might give different bond strengths. For primary samples (e.g., core samples from a subterranean formation) where this penetration is a potential issue, the primary sample can be allowed to soak in the drilling fluid for between 20 and 40 minutes. It is not necessary to soak impermeable samples (e.g., steel samples representing casing material) and these samples are just dipped into the drilling fluid and removed without soaking. In forming the illustrated sample 300, the sandstone 304 was dipped in the drilling fluid 306 for 30 minutes and hung for 30 minutes more to drip off excess fluid. The drilling fluid 306 was then scraped off leaving a visible thin coating of drilling fluid 306 on the sandstone 304. This process can be adjusted based on the formation and drilling fluid used but to ensure repeatability of the test, this information should be documented as a test parameter. Just as boundary conditions can be applied to theoretical analysis, coating thickness of drilling fluid 306 is an experimental control and can be varied. For example, a set method can be used so that the coating thickness can be held approximately constant.

Figure 4:
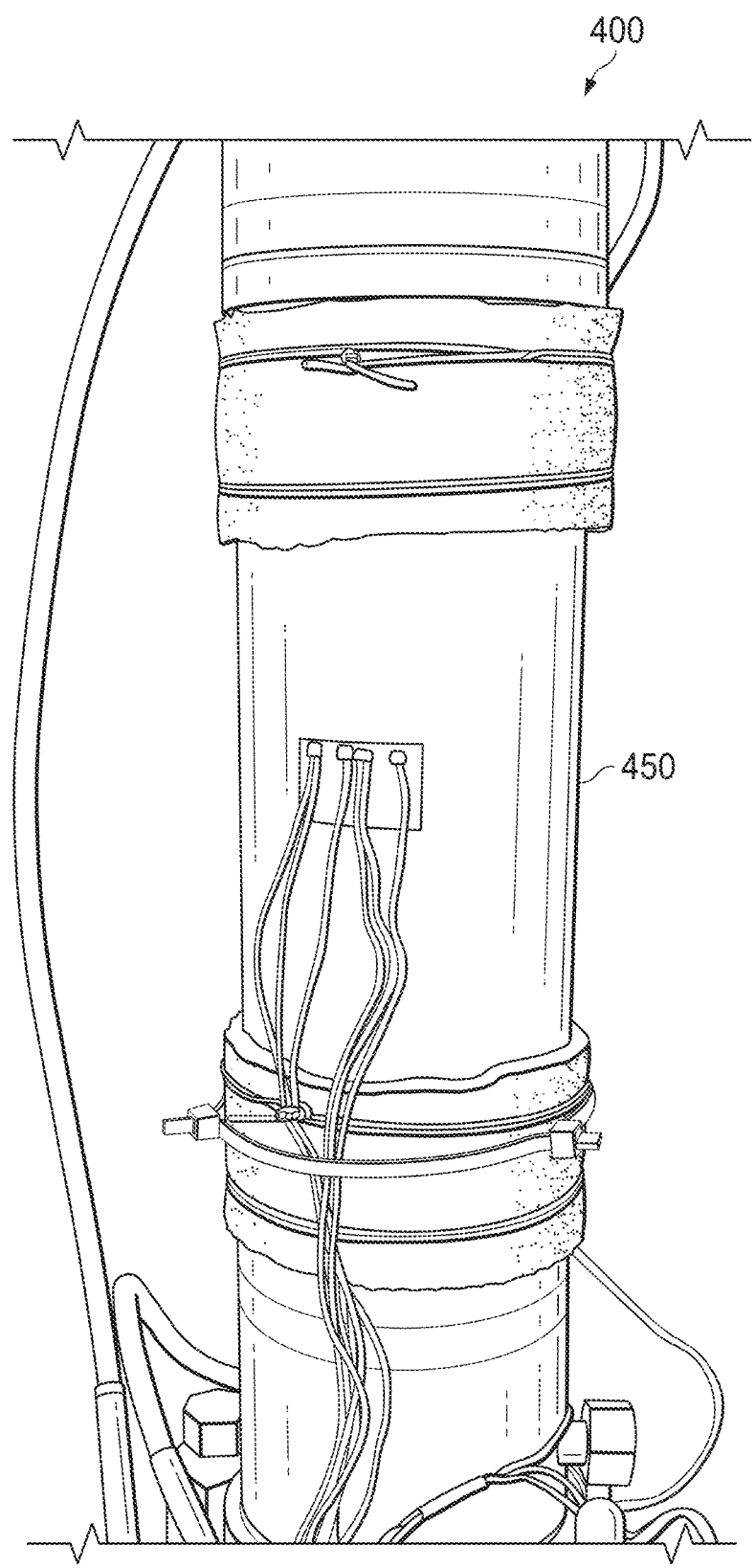
FIG. 4 is an illustration of an instrumented composite sample loaded in a tri-axial testing system.

Cement 102 is mixed with additives and water and cast to the cut core sample 104 in a cylindrical mold (not shown). The casting process forms a bonded connection 114 between the cement 102 and the core sample 104. The cement 102 is then cured. For example, the composite sample 100 was cured in a mold at 180 degrees F. and 3000 psi for 3 days. The cure temperature, pressure, and time can be varied for different cements. After curing, the cement and sandstone form a composite sample 100 that can then be trimmed to provide a length-to-diameter ratio of at least 2 with the bonded interface 106 approximately at the center of the composite sample 100 to have equal amounts of cement 102 and a core sample 104. Other length to diameter ratios can be used as long as they are compatible with the tri-axial testing machine, which is described in more detail below. The ends of the composite sample 100 are formed (e.g., molded or cut) to provide faces which are parallel and transverse to the axis of the composite sample 100. These faces can be significant in accurately measuring the s wave velocity and the p wave velocity of the composite sample 100. The composite sample 100 can be jacketed in a jacket copper sleeve under pressure. For example, this pressure can be 1000 psi. The purpose of the jacket is to prevent the confining fluid (oftentimes oil) to permeate into the sample. Epoxy jackets can also be used. A jacket is often not necessary during calibration of pure aluminum samples. As shown in FIG. 4, a jacket 450 is placed over the composite sample 100 as part of an instrumented composite sample 400.

Figure 5:
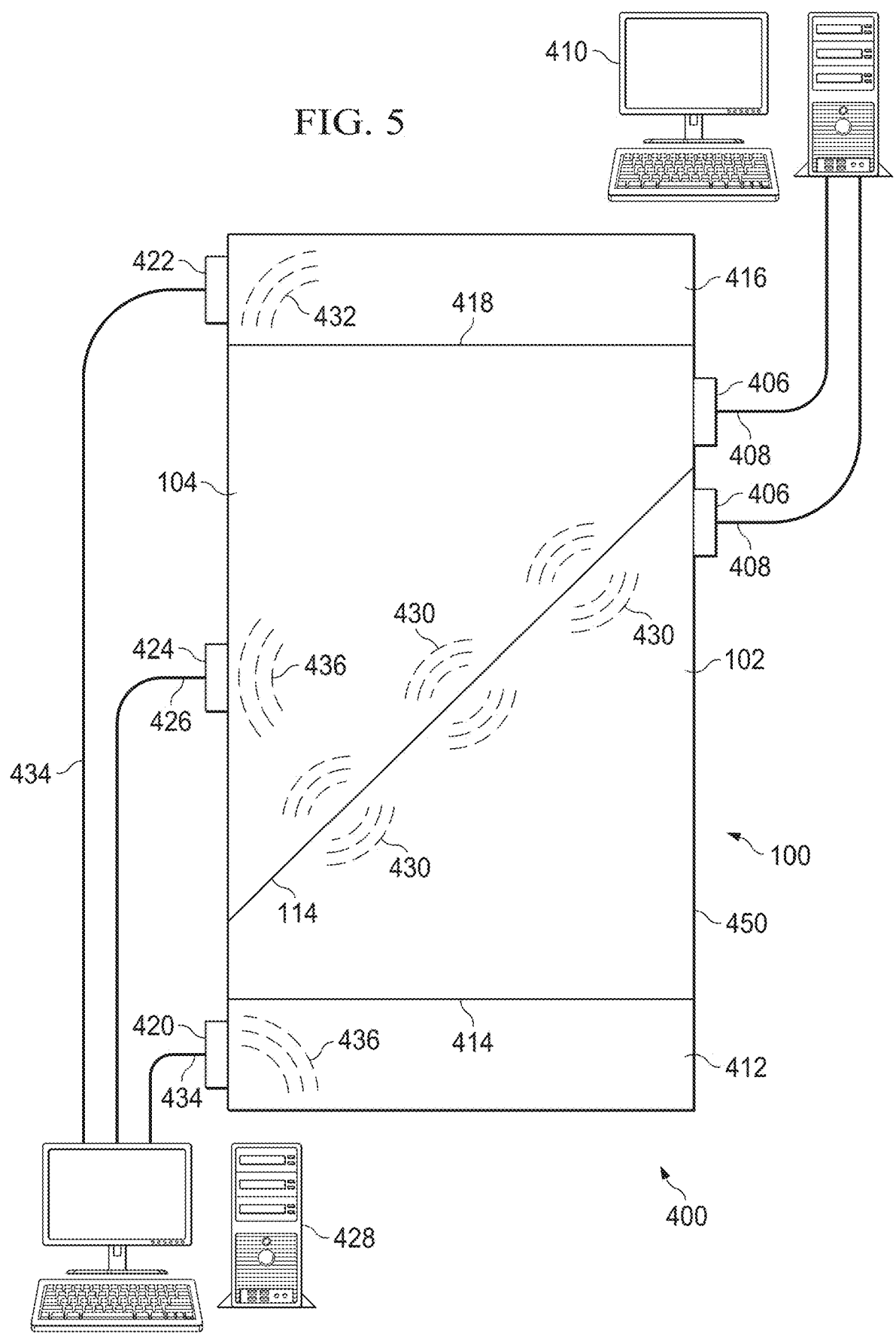
FIG. 5 is a schematic of an instrumented composite sample.

The composite sample 100 of cement 102 and sandstone 104 is prepared for testing as the instrumented composite sample 400 and further shown schematically in FIG. 5. The shear bond strength testing incorporates test data processing including the acquisition of acoustic transducer data and strain data at conditions representative of reservoir conditions. This test data is then post-processed to determine distinct phases leading to failure of the shear bond 114 of the composite sample 100.

Strain gauges 406 are attached to the composite sample 100. Wires 408 can be soldered or otherwise attached to the strain gauges 406. These wires 408 lead to a data acquisition system 410 for strain gauges. Changes in the length, or dimensions, of the composite sample 100 can be measured by the foil-resistance strain gauges 406 attached to the composite sample 100 in the vertical and horizontal directions. The Wheatstone bridge principle can be used for more accurate measurements of length changes. For example, several 1-XY36-6/120 strain gauges can be used for this purpose.

End caps can be attached on both axial ends of the composite sample 100. For example, a lower end cap 412 can be applied to the bottom surface 414 of the composite sample 100, and an upper end cap 416 can be applied to the top surface 418. The end caps 412, 416 are typically made of aluminum and can also have a diameter that corresponds to a diameter of the sample. The end caps 412, 416 can be approximately 1-2 inches in length and be used to help secure the sample in place in the pressure vessel and provide p wave and s wave acquisition using acoustic transducers.

Acoustic transducers are a type of acoustic sensor that convert electrical signals into ultrasound or vice versa. They can be located on the surface of or inside the lower and upper end caps 412, 416 or on the surface of the composite sample 100. Acoustic transducers 420, 422 can also be placed at various angles with respect to the shear bond interface 114. These transducers can be used to track p and s wave velocities through the composite sample 100. For instance, a first acoustic transducer 420 mounted in the lower end cap 412 can be used to transmit 436 an acoustic pulse and a second acoustic transducer 422 mounted in the upper end cap 416 receives 432 this acoustic pulse. The end caps can also include one p wave ultrasonic transducer and two s wave ultrasonic transducers. The transducers typically operate at 1 MHz, but any frequency can be used.

The transmitting acoustic pulse signal from the acoustic transducer can induce propagating p and s waves (shown schematically 436, 432) that travel from the first acoustic transducer 420 to the second acoustic transducer 422. The arrival time and polarization of this wave can be used to determine a travelling p wave velocity and a travelling s wave velocity through the composite sample 100 which also passes through the bonded interface 114. Wave polarization can be used to differentiate a p wave from an s1 and s2 wave. P waves have particle oscillations in the same direction as wave propagation, but for s waves (including s1 and s2 waves) the particle oscillations are perpendicular to the direction of wave propagation. Additionally, the s1 and s2 waves have particle oscillations that are perpendicular to each other which are sometimes referred to as in-plane and anti-plane shear wave polarizations. Typically, the p wave is much faster than the s waves. Deformation also affects these wave velocities and is discussed in more detail below. Changes in amplitude (Q value), wave dispersion, and frequency can be further observed to fingerprint the shear bond. For example, when two materials A and B have a similar value P for bond strength, they can only be identified or fingerprinted by values P1 and P2 for amplitude. Such an approach is analogous to using fingerprinting for identifying or re-identifying individuals.

As shown in FIG. 5, and described above, the acoustic transducers 420, 422 can be mounted directly to the end caps. They may also be located elsewhere on the composite sample 100. The acoustic transducers 420, 422 are connected via wires 434 to a data acquisition system 428 which provides signal processing and conditioning of the acoustic signals. Propagating wave velocities can be measured in each sample at ultrasonic frequencies (about 1 MHz) using a pulse transmission technique and these acoustic transducers.

In addition to measuring p and s wave speeds through the composite sample 100, sound waves 430 generated by defects, such as cracking, breaking, or tearing, of the microstructure of the composite sample 100 during deformation can also be detected. These sound waves 430 can also be referred to as radiated sound waves or acoustic emissions, and may be observed to fingerprint the nature of the shear bond 114 between the two materials (such as cement 102 and sandstone 104) of the composite sample 100. The count rate of the signal can also be used. A count rate is often referred to as acoustic emission wave counts at fixed time intervals. In this case it can represent counts above 1000 counts per every 2 second intervals. The intensity, frequency, and dispersion of emitted acoustic waves 430 is used as a descriptor of the shear bond 114. These sound waves 430 are received using additional acoustic transducers 424, located at the top end cap 416 of the specimen. In FIG. 5, the acoustic transducer 424 are schematically shown on the surface of the specimen or on the jacket 450 but they can be located anywhere convenient, such as in the end caps of the specimen. During deformation, these defects cause sound waves 430 to generate propagating waves 436 which are detected by the acoustic transducer 424. While only one acoustic transducer 424 is shown in FIG. 5, more than one can be used. These transducers are passive as they only listen for sounds. In contrast, the transducers used for p and s wave velocity are active transducers.

Figure 6:
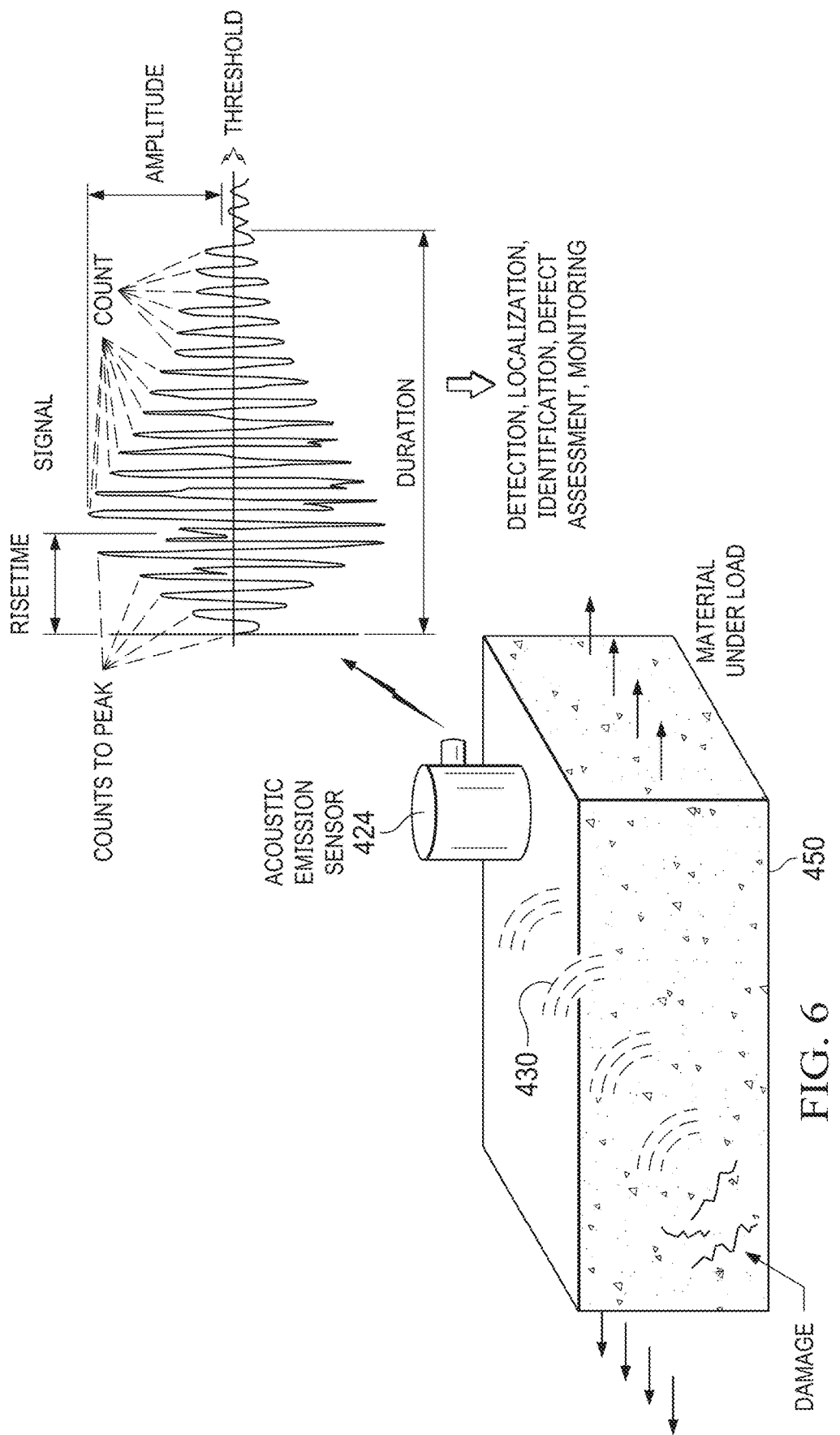
FIG. 6 is an illustration of the function of an acoustic emission transducer.

FIG. 6 illustrates the basic functionality of the acoustic transducer 424. The acoustic transducer 424 is shown on the surface of the composite sample 100, however they may also be located external to the instrumented composite sample 400. For example, the acoustic transducers 424 can be a part of the tri-axial testing machine. Sound waves 430 generated by defects propagate to the acoustic transducer 424. The acoustic transducers 424 are connected via wires 426 to a data acquisition system 428 which provides signal processing and conditioning of the received 436 acoustic signals. This acquisition system can be the same as the one for the p and s wave velocities or separate. Typically, there are different acoustic transducers for p and s wave velocity 420, 422, and acoustic emissions 424. However, this is not required. There can be cases where the same transducers for p and s wave velocity 420, 422 and acoustic emissions 424 are used. The signal is conditioned and analyzed to detect, localize, identify defects and monitor for their presence. The signal can be used to infer information on signal counts to peak, signal rise-time, signal amplitude, signal duration, signal count, and a signal threshold.

Figure 7:
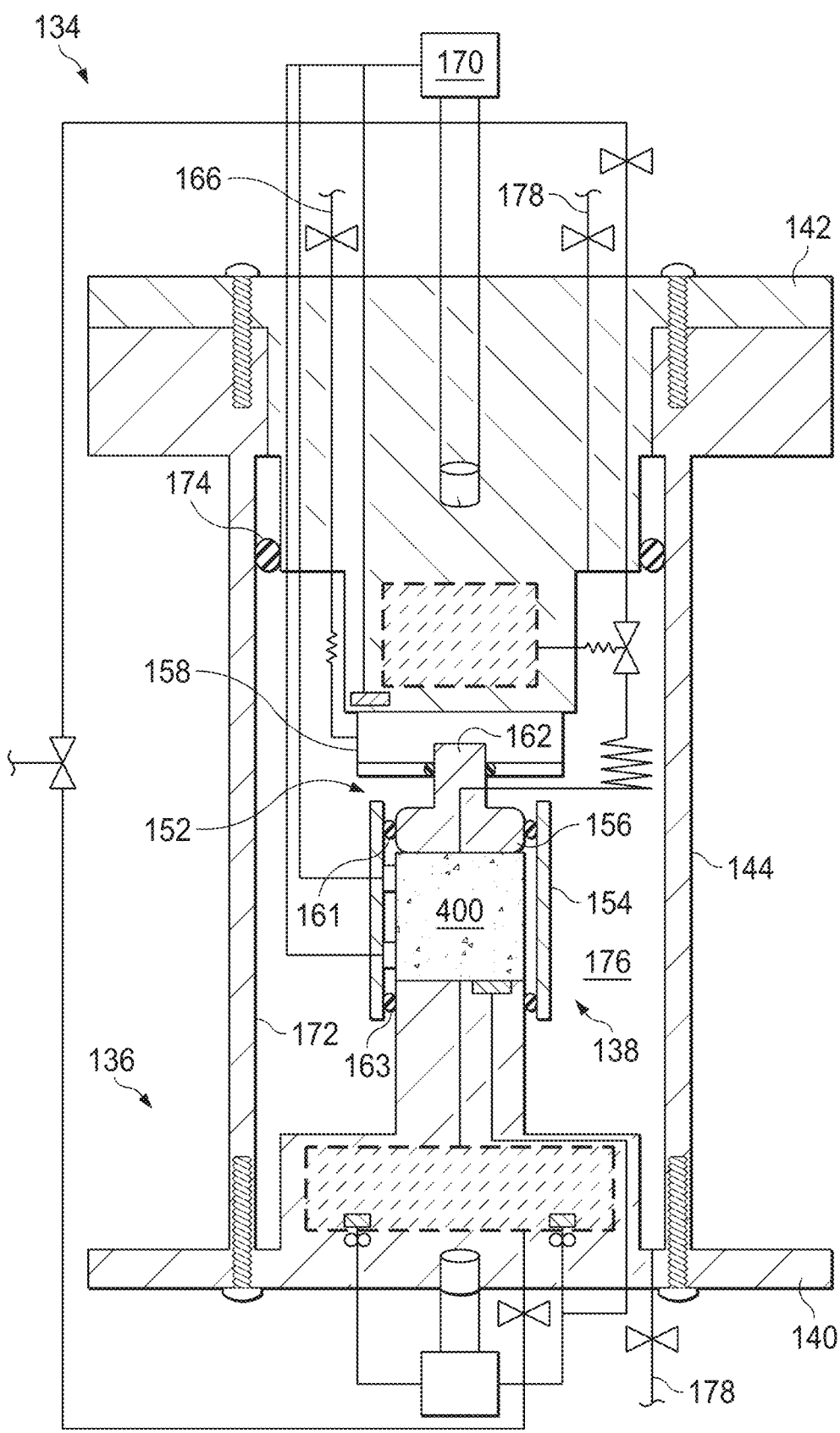
FIG. 7 is a schematic of a tri-axial testing system.

The instrumented composite sample 400 is then loaded in a tri-axial testing system such as the NER Autolab 3000 to find its bond strength along with other mechanical properties. Referring back to FIG. 4, the instrumented composite sample 400 is shown loaded in a pressure vessel of a tri-axial testing system. For example, the implementation of a tri-axial testing system for simulating reservoir conditions is described in U.S. patent application Ser. No. 16/393,016 ("Testing Petro-Physical Properties Using a Tri-axial Pressure Centrifuge Apparatus") filed on Apr. 24, 2019. Shown in FIG. 7, the machine typically contains a test cell 134 with a casing 136 containing a sample holder 138. The sample holder 138 is configured to hold the instrumented composite sample 400. The sample holder 138 includes a piston assembly 152 and an electrical jacket 154 extending between the piston assembly 152 and the base 140 of the casing 136. The electrical jacket 154 provides electrical communication to the strain gauges 406, acoustic transducers 420, 422, 424, and any other data measured. Piston assembly 152 includes a piston member 156, and a piston fluid chamber 158. An axial pressure fluid supply line 166 supplies fluid to piston fluid chamber 158. A fluid chamber base 160 has an opening through which the stem 162 of piston member 156 extends. An end face of piston member 156 engages the upper end cap 416 of the instrumented composite sample 400. Base 140 has an end face that engages the lower end cap 412 instrumented composite sample 400. Instrumented composite sample 400 is contained between the end face of the piston member 156 and the end face of base 140. As fluid is added to the piston fluid chamber 158 by way of axial pressure fluid supply line 166, the end face of piston member 156 applies axial force (for example axial force 206) on the upper end cap 416 of the instrumented composite sample 400, inducing axial stress (for example axial stress 210) in the instrumented composite sample 400.

The sample holder 138 can also include an electrical jacket 154. The electrical jacket 154 is a tubular member that surrounds the instrumented composite sample 400. A piston seal 161 forms a seal between the inner bore of a first end of electrical jacket 154 and an outer surface of piston member 156. A base seal 163 forms a seal between the inner bore of a second end of the electrical jacket 154 and an outer surface of base 140.

As previously discussed, the casing 136 includes the base 140, the end cap 142, and the body 144 extending between the base 140 and the end cap 142. The body 144 is a generally cylindrical member with an inner bore 172. The base 140 and the end cap 142 are bolted to the body 144 of the casing 136. A casing seal 174 limits the flow of fluid between the inner surface of inner bore 172 and the outer surface of the reduced diameter portion of end cap 142. The base 140, the end cap 142, and the body 144 define a cell chamber 176. Confining pressure fluid supply lines 178 delivers fluid to cell chamber 176 for applying confining pressure (for example confining pressure 204) on the instrumented composite sample 400.

The tri-axial testing machine is connected to experimental equipment that can include a confining-pressure vessel, an axial stress controller, a pressure pump and transfer vessel for controlling pore pressure, a digital oscilloscope, a pulse generator, ultrasonic transducers attached at the top, bottom, a data-acquisition device, and a computer. Resistive strain gauges can also be used to measure deformation.

After the machine is prepared for testing, a constant confining pressure 204 is typically applied and calibrations can be conducted. After calibration, the piston 156 of the tri-axial test system is loaded at a constant rate to compress the sample axially, thus generating an axial force 206 and an axial stress 210 (see FIG. 2).

Since the system typically switches between acquiring acoustic emission data and velocity data, the loading rate should be kept low enough that the system can acquire all necessary data (e.g., a loading rate of 0.01 MPa/second or less). Note that when the main consideration is stability of the instrument, recommended loading rates for unconfined tests are typically 0.005-0.02 MPa/second. Velocities, strain gauge deformation of the sample, and acoustic emission can be measured every 2-4 seconds. However, measurements can be taken at other time intervals and using other loading rates.

Failure, and more specifically shear bond failure, in a test specimen is recognized when volumetric strain reaches a maximum and subsequently begins to decrease as axial stress increases. Volumetric strain can be measured from the strain gauge and defined as two times the radial strain plus the vertical strain. Both the radial strain and the vertical strain are measured from the strain gauge. In addition, more information can be determined about the failure of the specimen than just a single number representing the shear bond strength. This is achieved by computing the p and s wave velocity and acoustic emissions of a test specimen during deformation and during failure of the test specimen as previously described. The use of these methods individually or in tandem with measurements of the differential stress required for the debonding of the two materials gives additional descriptors and insight in to the nature of the interface between the materials. Furthermore, the use of these methods can be used for customizing sample preparation techniques based on rock formation or changing the stress regimes based on rock formation or cement formulation. As previously mentioned, obtaining consistent results requires keeping the diameter to length ratio of the samples constant and maintaining the same or at least substantially similar surface roughness.

After the test is complete, data analysis can be performed to interpret the bond strength and other mechanical properties. The data can be gathered and plotted in a spreadsheet program, such as Microsoft Excel, for a descriptive analysis. This analysis helps determine how the samples failed by identifying individual regions as mentioned below. Additionally, calculations are done in a programming language, such as Matlab, for mechanical properties and bond strength. These are merely examples, and the calculations discussed can be also performed in other software packages.

Figure 8:
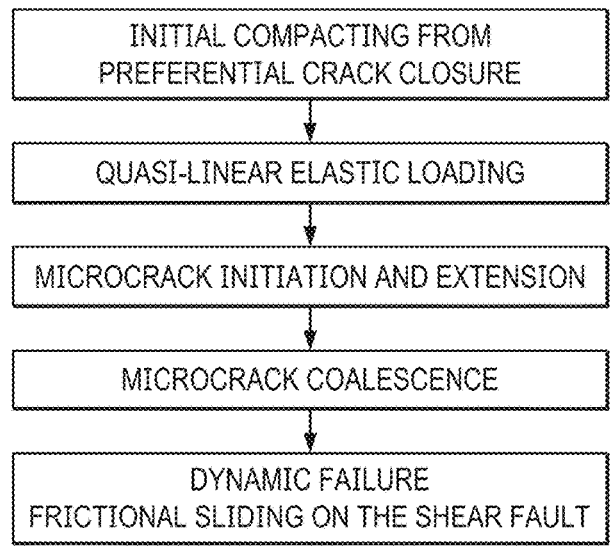
FIG. 8 is a flow chart showing a characterization of the five testing regions.

As mentioned previously, comparison of the acoustic emissions and the changes in p and s wave velocities during deformation provide considerable insight into the mechanical processes taking place. As a result, the deformation history of a test specimen can be divided into five broad regions and are summarized in FIG. 8. The first region (I) is initial compaction phase, the second region (II) is quasi-linear elastic loading phase, the third region (III) is microcrack initiation and extension phase, the fourth region (IV) is microcrack coalescence phase leading to the development of macrocracks, and the fifth region (V) is a dynamic failure phase with frictional sliding on the shear fault phase formed by coalescence of the macrocracks. These phases are described below with reference to actual testing events.

Figure 9:
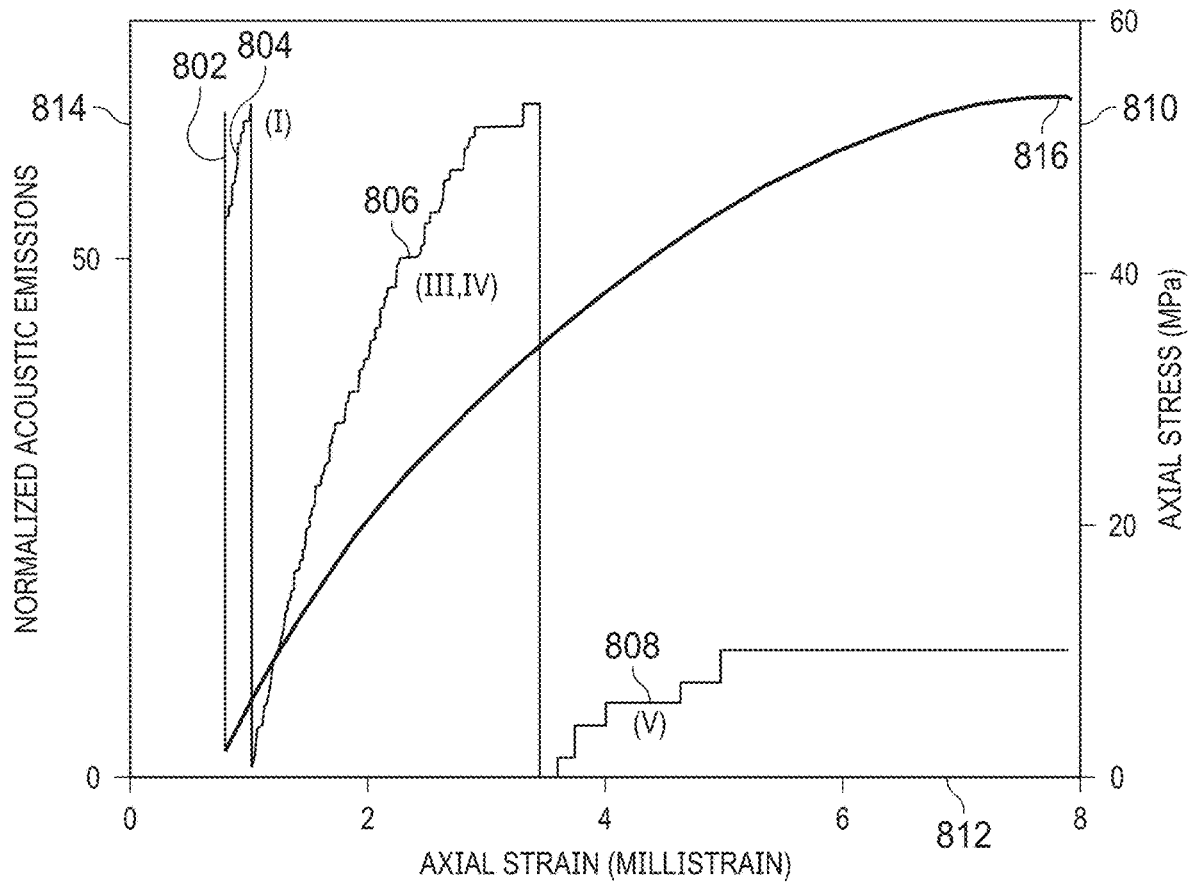
FIG. 9 is a chart showing acoustic emissions relative to axial strain for pure cement.

Referring to FIG. 9, an axial stress 810 is applied by the tri-axial testing machine. Axial strain 812, acoustic emissions 814, and p wave velocities 908 are measured. As the applied axial stress 810 increases, the specimen undergoes the five phases associated with regions (I), (II), (III), (IV), and (V) until shear bond failure occurs. The maximum axial stress 816 attained defines the peak strength of the sample or bond. Failure strength is when the volumetric strain rolls over and is defined as shear strength once the failure plane is verified by observing the failed sample.

As the sample is first loaded, the specimen undergoes initial compaction that results from the preferential closure of cracks normal to the principal compression axes. This defines the first phase (region I) and is identified by acoustic emissions that start off low and increase with stress and strain and s and p wave velocities that increase as axial stress 810 is applied.

Figure 10:
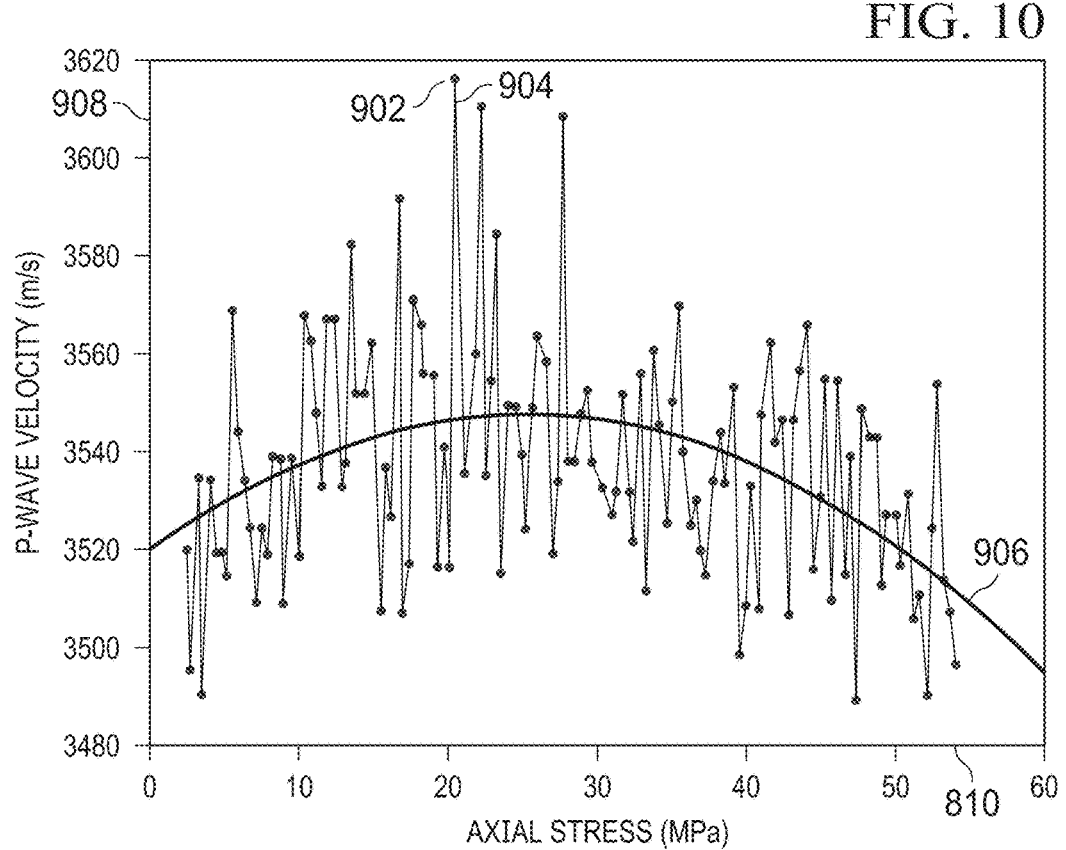
FIG. 10 is a chart showing p wave velocity data relative to axial stress for pure cement.
Figure 13:
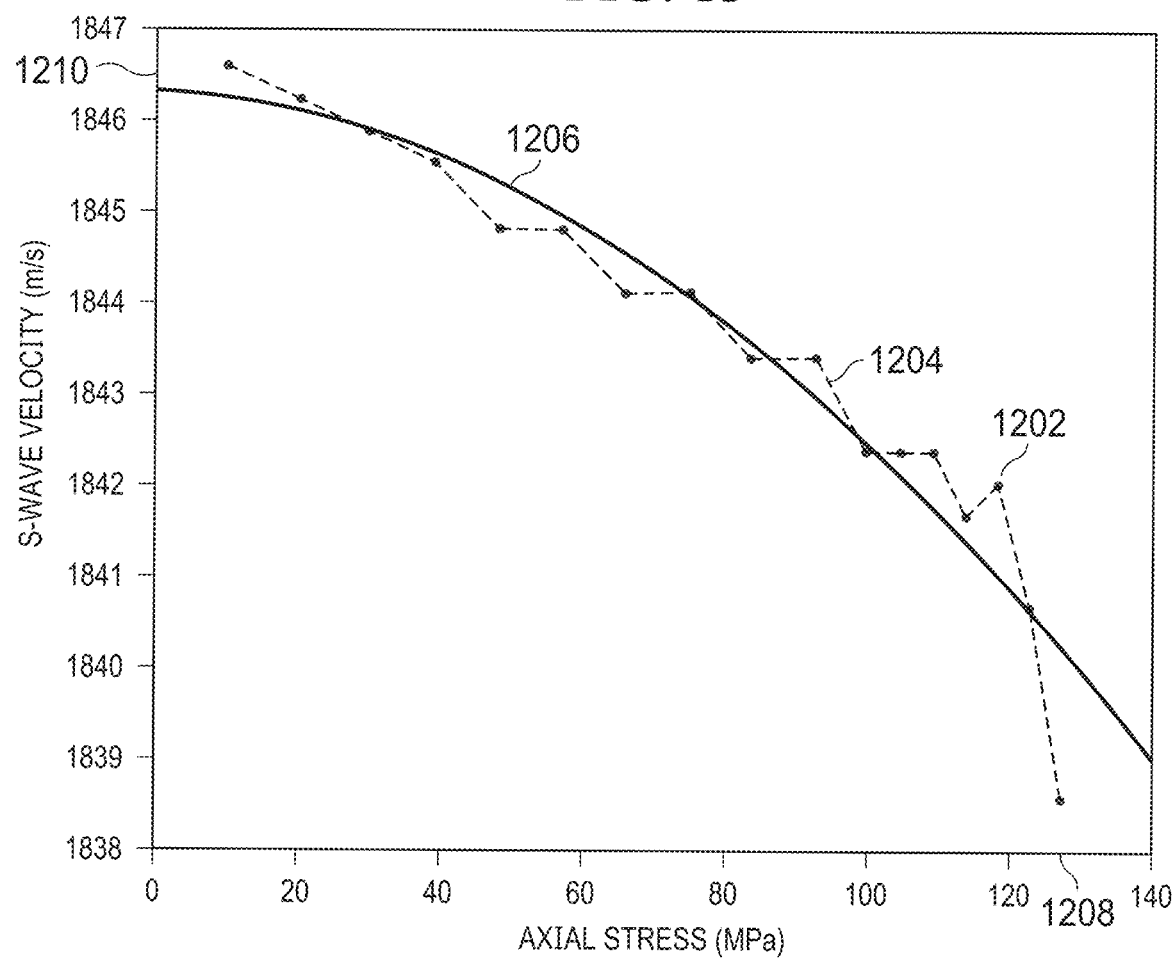
FIG. 13 is a chart showing s wave velocity data relative to axial stress for polymeric cement.

This phenomena is shown in FIGS. 9 and 10 for testing of a pure cement sample. The pure cement sample is a monolithic casting of cement in a cylindrical mold of 2 inch diameter by 4.5 inches in length, but other sizes can be used. The pure cement sample can be a solid core of cement. Upon loading, the initial compaction phase (region I) is detected by the increase in acoustic emissions 804. Increasing p wave velocity as a function of axial stress 810 is shown in FIG. 10 where the data points 902 are interpolated 904 and a fitting algorithm or trend is used to determine a best fit 906. In this case, p, s1 and s2 waves are measured and collected, but only the results for p wave velocities are shown. Oftentimes velocity data for p waves can be less noisy resulting in a better measurement that when using s waves. However, this is not always the case. For example, as will be described in further detail below, FIG. 13 shows results for s wave velocities which are less noisy than p wave velocities. In some cases, one can infer a trend visually using the raw data without a need for curve-fitting or mathematical smoothing, but in other cases a polynomial curve fit, such as a 2nd order polynomial fit can be applied. A 2nd order polynomial fit has been applied to the results shown in FIG. 10. As evident from FIG. 10, the best fit 906 of the p wave velocity increases as axial stress 810 is applied.

Figure 11:
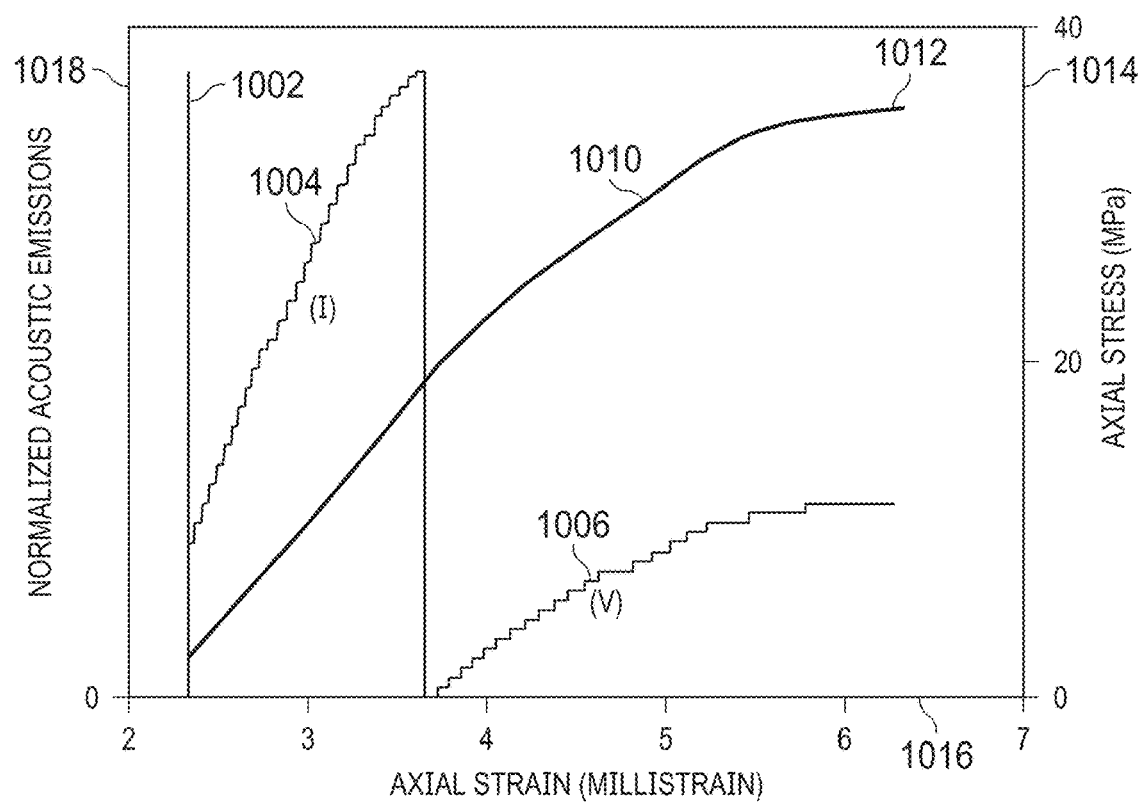
FIG. 11 is a chart showing acoustic emission relative to axial strain data for a cement-sandstone composite sample with oil-based mud applied at the bonding interface.
Figure 12:
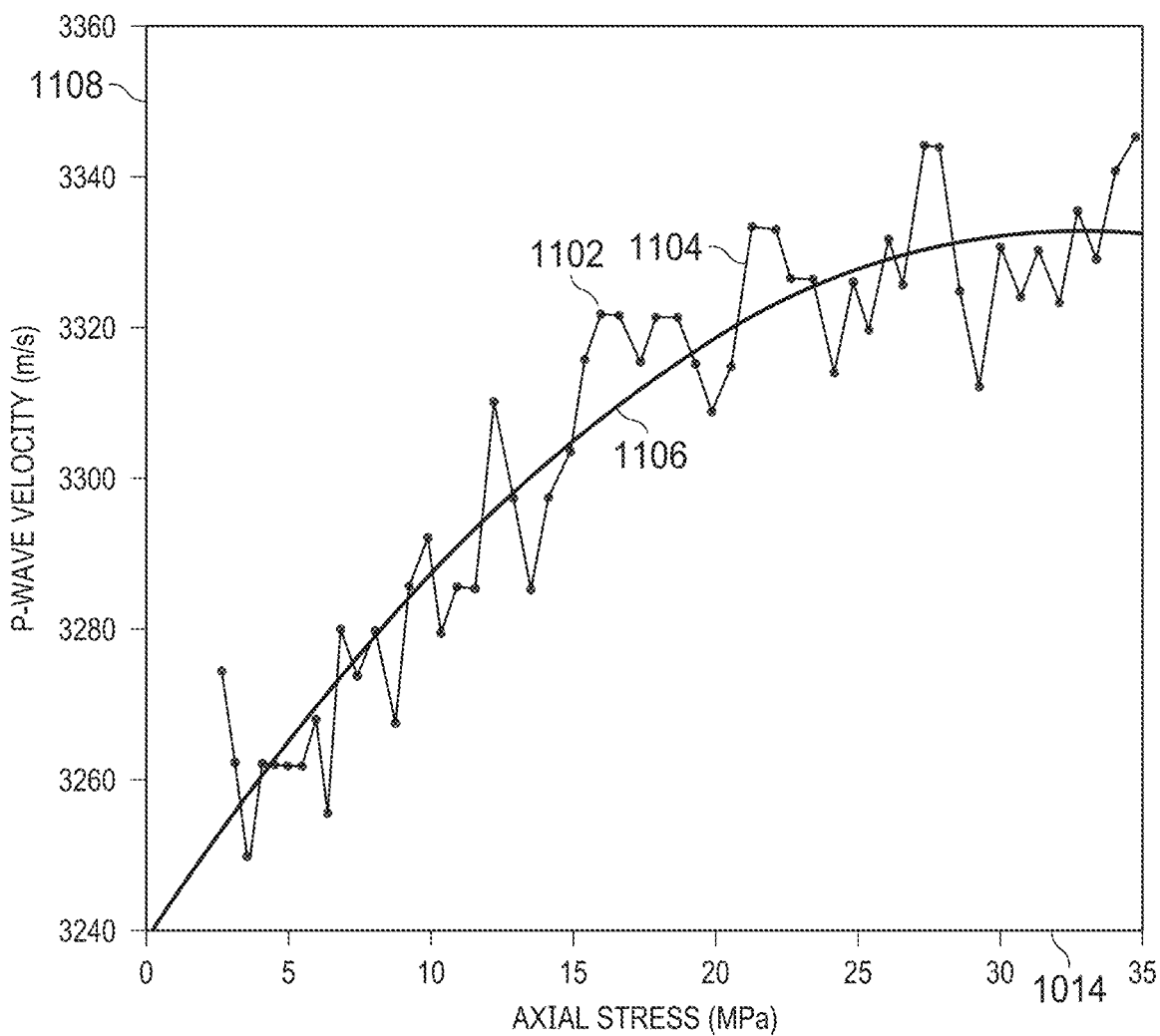
FIG. 12 is a chart showing p wave velocity data relative to axial stress for a cement-sandstone composite sample with oil-based mud applied at the bonding interface.

FIGS. 11 and 12 show results for the case of the cement-sandstone composite sample 300 with oil-based mud applied as a drilling fluid 306 at the bonded interface 306 as shown in FIG. 3. The rise in acoustic emissions 1004 marks the initial compaction phase (region I) and occurs over a larger axial strain 1016 and axial stress 1010, 1014 than the case for pure cement in FIG. 9. Similarly, FIG. 12 shows an increase in p wave velocity where the data points 1102 are again interpolated 1104 and a fitting algorithm is used to determine a best fit 1106.

Note that in some cases, acoustic emission peaks 802, 1002, are recorded prior to the test event, but these peaks can be ignored, as they do not relate to a physical event. Rather, these peaks relate to initiating the testing setup.

As axial stress is further increased, the sample passes through a quasi-linear elastic phase (region II) with slowly changing (but still increasing) p and s wave velocity. This second phase (region II) may not be captured by either velocity or acoustic emission depending how long it lasts.

The quasi-linear elastic phase (region II) is not distinguishable for pure cement in FIG. 9 nor it is distinguishable for the cement-sandstone composite sample 300 with oil-based mud applied as a drilling fluid 306 at the bonded interface 306 in FIG. 11. The slowly increasing p wave velocities are, however, apparent in FIGS. 10 and 12. However, this region is very hard to detect because it is often very short-lived. This can make it hard to identify and distinguish one region from the next. In FIG. 10, velocities reach a peak and remain substantially constant (or at least only slowly change) between a stress ranges of 24-26 MPa. This substantially constant region represents the quasi-linear elastic phase (region II).

As the sample is further loaded, the sample undergoes microcrack initiation and extension. This defines the third phase (region III) and is identified by a velocity decrease, an increase in acoustic emissions, and a strain increase with axial stress. In this phase (region III), cracks are growing predominantly parallel to the principal compression axis, with an increasing rate of acoustic emission activity.

FIG. 9 shows a rise in acoustic emissions 806 associated with microcrack initiation and extension phase (region III) for pure cement. FIG. 10 shows the p wave velocity best fit 906 reaching a maximum and beginning to decrease around 25 MPa. This decrease in p wave velocity is associated with microcrack initiation and extension phase (region III). Conversely, the cement 302 and sandstone 304 composite sample with oil-based mud applied as a drilling fluid 306 at the bonded interface 308 does not show this region in the acoustic emission data, but there is a maximum in the p wave best fit 1106 around 32 MPa—just prior to failure.

As the sample is further loaded, the microcracks extended in region III coalesce to form macrocracks. This region is called macrocrack formation and propagation phase. This phase (region IV) is identified by a sharp decrease in p and s wave velocity, a strain increase with stress, and high levels of acoustic emissions. In some instances, the acoustic emissions exceeding the capacity of the acoustic sensor. This can cause acoustic saturation of the acoustic sensor, depending on the sensitivity and dynamic range of the acoustic transducer. FIG. 9 shows this region 806 grouped with the microcrack formation and propagation phase (region III). However, similar to the quasi-linear elastic phase (region II), this region is also very hard to detect because it is often very short-lived. This can cause a blending of regions and makes it hard to identify and distinguish one region from the next.

As the sample is further loaded, the sample undergoes frictional sliding on the shear fault 808. This fifth and final phase (region V) is identified by acoustic emissions remaining constant because microcracks have been saturated, while at the same time the accumulating damage hinders p and s wave propagation. This region is usually hard to observe as it occurs at the post-microcracking stage. The maximum axial stress 1012 attained defines the peak strength of the sample or bond.

As previously noted, it is often difficult to distinguish all five phases (regions I-V), as some regions might be very short lived (for example, the second phase (region II) and fourth phase (region IV)) in comparison to its adjacent regions: first phase (region I), third phase (region III), and fifth phase (region V).

The first phase (region I) of initial compaction may be absent at higher confining stresses, due to stiff and dense materials or materials that already have closed microcracks. For example, the first phase (region I) of initial compaction is absent in a polymeric cement case as shown in FIG. 13 which shows only the third phase (region III) and fourth phase (region IV) of microcracking and a fifth phase (region V) of sliding. FIG. 13 shows a decrease in s wave velocity 1210 where the data points 1202 are again interpolated 1204 and a fitting algorithm or trend is used to determine a best fit 1206 versus axial stress 1208. As previously mentioned p, s1 and s2 waves can be measured and collected, however p wave velocity measurements oftentimes can be less noisy in comparison to s wave velocity measurements. In addition, it can be redundant to visualize and analyze each of these three wave velocities so only one is required during analysis. However, in the results shown in FIG. 13, the s wave velocity data was less noisy than the p wave velocity data and was used instead. The decrease in this best fit 1206 velocity is associated with the third, fourth, and fifth phases (regions III, IV, and V). The initial compaction phase (region I) is absent as there is no increase in velocity observed. A quasi-linear elastic phase (region II) is also not distinguishable for this case.

Similarly, the third, fourth, and fifth phases (regions III, IV, and V) can combine when there is a pre-existing weak bedding plane in a sample. For example, in an inclined composite sample such as the one shown in FIG. 11 (cement-sandstone composite sample 300 with oil-based mud applied as a drilling fluid 306 at the bonded interface 308), only two distinct events are seen, the first phase 1004 (region I) of initial compaction and the fifth phase 1006 (region V) of frictional sliding. Notably, the second, third, and fourth phases (regions II, III, and IV) regions are not distinguishable.

The entire testing process can be repeated by varying the cement, introducing or changing cement additives, changing the formation, and by adding or changing drilling fluids. As a result, one can effectively and repeatedly understand the bond strength of cement to the surrounding subterranean formations. Knowledge of this bond strength and interaction with the cement itself can help to provide zonal isolation in a drilling operation. The cement-formation interface can thus be improved to withstand stresses during drilling, completion/stimulation and production phases. This testing method in combination with setting the bond angle between the cement and the subterranean formation sample at 60 degrees is easier, faster, more repeatable, and cheaper.

A number of embodiments of the systems and methods have been described. Nevertheless, it will be understood that various modifications may be made without departing from the spirit and scope of this disclosure. Accordingly, other embodiments are within the scope of the following claims.

What is claimed is:

1. A method for testing shear bond strength of cement with a sample under downhole conditions, the method comprising:

forming a bonding surface of the sample oriented at an angle between 50 and 70 degrees from a plane perpendicular to a longitudinal axis of the sample;

forming a composite sample by bonding the cement to the sample with the cement in contact with the bonding surface of the sample;

installing the composite sample in a cell casing, installing the cell casing in a tri-axial testing machine;

applying a first pressure to the composite sample, wherein the first pressure is greater than an environmental pressure;

applying an axial pressure to the cell casing and sample that is greater than the first pressure;

measuring a wave velocity of the composite sample using a first acoustic transducer and a second acoustic transducer;

measuring an acoustic emission emitted by the composite sample using a third acoustic transducer; and identifying a failure of the composite sample based on the measured acoustic emission and the measured velocity.

2. The method of claim 1, further comprising coating the sample with a drilling fluid before forming the composite sample.

3. The method of claim 1, wherein measuring the wave velocity of the composite sample comprises measuring a p wave velocity or an s wave velocity of the composite sample using the first acoustic transducer and the second acoustic transducer.

4. The method of claim 3, wherein measuring the acoustic emission emitted by the composite sample comprises measuring an intensity, frequency, or dispersion of acoustic waves emitted by the composite sample using the third acoustic transducer.

5. The method of claim 4, wherein identifying the failure of the composite sample based on the measured acoustic emission and the measured velocity comprises identifying an initial compaction phase of axial compression by detecting an increase in the measured acoustic emissions relative to an ambient condition and an increase in the measured p wave velocity, the measured s wave velocity, or both.

6. The method of claim 4, wherein identifying the failure of the composite sample based on the measured acoustic emission and the measured velocity comprises identifying a quasi-linear elastic phase of axial compression by detecting a decrease in the measured acoustic emissions and a decrease in the measured wave velocity.

7. The method of claim 4, wherein identifying the failure of the composite sample based on the measured acoustic emission and the measured velocity comprises identifying a micro-crack initiation and extension phase of axial compression by detecting an increase in the measured acoustic emissions.

8. The method of claim 4, wherein identifying the failure of the composite sample based on the measured acoustic emission and the measured velocity comprises identifying a crack coalescence and dynamic failure phase of axial compression by detecting an increase in the measured acoustic emissions and a decrease in the measured p wave velocity and the measured s wave velocity.

9. The method of claim 4, wherein identifying the failure of the composite sample based on the measured acoustic emission and the measured velocity comprises identifying a frictional sliding phase by detecting a decrease in a load bearing capacity of the composite sample, an increase in the measured acoustic emissions, or both.

10. The method of claim 4, further comprising measuring a strain of the composite sample using a strain gauge located on the composite sample.

11. The method of claim 4, further comprising determining the shear bond strength of the cement.

12. The method of claim 3, wherein forming the composite sample comprises:
trimming the lower end surface to be flat and perpendicular to the longitudinal axis;
trimming the composite sample to achieve a length of the composite sample to a diameter of the composite sample ratio greater than or equal to 2; and
trimming the composite sample to be 40-60% cement and 40-60% sample.

13. The method of claim 1, wherein identifying the failure of the composite sample based on the measured acoustic emission and the measured velocity comprises identifying the failure based on a magnitude or a rate of change of the measured velocity as a function of an axial stress of the composite sample.

14. The method of claim 1, wherein identifying the failure of the composite sample based on the measured acoustic emission and the measured velocity comprises identifying the failure based on an intensity of the measured acoustic emissions and a rate of change of measured velocity.

15. The method of claim 1, further comprising switching between measuring the wave velocity of the composite sample and measuring the acoustic emission emitted by the composite sample.

16. The method of claim 1, further comprising determining a curve fit of the measured wave velocity as a function of axial stress, wherein identifying the failure of the composite sample based on the measured acoustic emission and the measured velocity comprises identifying the failure of the composite sample based on the determined curve fit of the wave velocity.

17. A system for testing a composite sample formed of a cement bonded with a primary sample to identify a shear bond strength of the cement with the primary sample, the system comprising:
a first acoustic transducer;
a second acoustic transducer;
a third acoustic transducer;
a strain gauge; and
a computer electrically connected to the first, second, and third acoustic transducers and the strain gauge;
wherein the first acoustic transducer and the second acoustic transducer are configured to measure a p wave velocity or an s wave velocity;
wherein the third acoustic transducer is passive and configured to measure an acoustic emission emitted by the composite sample using a third acoustic transducer; and
wherein the computer is operable to identify a failure of the composite sample based on the measured acoustic emission and the measured p or s wave velocity.

18. The system of claim 17, further comprising:
a first end cap attachable to the composite sample with the first acoustic transducer mounted on the first end cap; and
a second end cap attachable to the composite sample with the second acoustic transducer mounted on the second end cap.

19. The system of claim 17, wherein the first acoustic transducer is configured to transmit a signal and the second acoustic transducer is configured to receive the signal.

20. The system of claim 19, further comprising a cylindrical casing, wherein the strain gauge is located on an outer surface of the cylindrical casing, and wherein the third acoustic transducer is mounted on the first end cap.

21. The system of claim 17, wherein the computer is operable to identify the failure based on a magnitude or a rate of change of at least one of the measured p wave velocity and the measured s wave velocity as a function of an axial stress of the composite sample.

22. The system of claim 17, wherein the computer is operable to identify the failure based on an intensity of the measured acoustic emissions and a rate of change of at least one of the measured p wave velocity and the measured s wave velocity.

23. The system of claim 17, wherein the computer is further operable to switch between measuring the wave velocities of the composite sample and measuring the acoustic emission emitted by the composite sample.

24. The system of claim 17, wherein the computer is further operable to determine a curve fit of at least one of the measured p wave velocity and the measured s wave velocity as a function of axial stress, wherein the computer is operable to identify the failure of the composite sample based on the determined curve fit of the at least one of the measured p wave velocity and the measured s wave velocity.

25. The system of claim 17, wherein the computer is operable to identify the failure of the composite sample as an initial compaction phase of axial compression by detecting an increase in the measured acoustic emissions relative to an ambient condition and an increase in the measured p wave velocity, the measured s wave velocity, or both.

26. The system of claim 17, wherein the computer is operable to identify the failure of the composite sample as a quasi-linear elastic phase of axial compression by detecting a decrease in the measured acoustic emissions and a decrease in at least one of the measured p wave velocity and the measured s wave velocity.

* * * * *